United States Patent
Lunn et al.

(10) Patent No.: US 9,345,467 B2
(45) Date of Patent: May 24, 2016

(54) ANCHOR ASSEMBLY

(75) Inventors: Richard Lunn, Kingston, MA (US);
David A. Paulk, Hopedale, MA (US);
Thomas C. May, Wrentham, MA (US);
Steven Astorino, Norton, MA (US)

(73) Assignee: Smith & Nephew, Inc., Memphis, TN (US)

(*) Notice: Subject to any disclaimer, the term of this patent is extended or adjusted under 35 U.S.C. 154(b) by 811 days.

(21) Appl. No.: 12/259,106

(22) Filed: Oct. 27, 2008

(65) Prior Publication Data

US 2009/0112270 A1    Apr. 30, 2009

Related U.S. Application Data

(60) Provisional application No. 60/982,521, filed on Oct. 25, 2007, provisional application No. 60/986,342, filed on Nov. 8, 2007.

(51) Int. Cl.
*A61B 17/04*    (2006.01)

(52) U.S. Cl.
CPC ..... *A61B 17/0401* (2013.01); *A61B 2017/0403* (2013.01); *A61B 2017/044* (2013.01); *A61B 2017/0412* (2013.01); *A61B 2017/0414* (2013.01); *A61B 2017/0427* (2013.01); *A61B 2017/0453* (2013.01)

(58) Field of Classification Search
CPC ............... A61B 2017/0425; A61B 2017/0412; A61B 2017/0453
USPC ........................ 606/232, 321; 411/16, 18, 21
See application file for complete search history.

(56) References Cited

U.S. PATENT DOCUMENTS

| | | | |
|---|---|---|---|
| 254,473 A | | 3/1882 | Gates |
| 3,187,620 A | * | 6/1965 | Fischer ........................ 411/80.5 |
| 3,268,965 A | | 8/1966 | Arthur |
| 4,636,121 A | * | 1/1987 | Miller ............................. 411/21 |
| 4,750,492 A | | 6/1988 | Jacobs |
| 4,870,957 A | | 10/1989 | Goble et al. |
| 4,927,421 A | | 5/1990 | Goble et al. |
| 5,037,422 A | | 8/1991 | Hayhurst et al. |
| 5,100,417 A | | 3/1992 | Cerier et al. |
| 5,102,421 A | | 4/1992 | Anspach, Jr. |
| 5,141,520 A | | 8/1992 | Goble et al. |

(Continued)

FOREIGN PATENT DOCUMENTS

| | | |
|---|---|---|
| DE | 200007777 U1 | 8/2000 |
| DE | 102008016607 A1 | 7/2009 |

(Continued)

OTHER PUBLICATIONS

International Search Report and Written Opinion for PCT/US2008/081342 Dated Feb. 26, 2009.

(Continued)

*Primary Examiner* — David Bates
(74) *Attorney, Agent, or Firm* — Norman F. Hainer, Jr.

(57) ABSTRACT

The present disclosure relates to an anchor assembly. The anchor assembly includes an anchor defining a cavity and an opening to the cavity and an insertion member configured for arrangement within the anchor cavity. The insertion member includes a body having a proximal end portion and a flat distal end portion, and a head coupled to the proximal end portion of the body. A method of tissue repair and other anchor assemblies are also disclosed.

28 Claims, 7 Drawing Sheets

(56) References Cited

U.S. PATENT DOCUMENTS

| | | | |
|---|---|---|---|
| 5,152,790 A | 10/1992 | Rosenberg et al. | |
| 5,156,616 A | 10/1992 | Meadows et al. | |
| 5,176,682 A | 1/1993 | Chow | |
| 5,258,016 A | 11/1993 | DiPoto et al. | |
| 5,268,001 A | 12/1993 | Nicholson et al. | |
| 5,356,435 A | 10/1994 | Thein | |
| 5,370,662 A | 12/1994 | Stone et al. | |
| 5,376,119 A | 12/1994 | Zimmermann et al. | |
| 5,383,905 A | 1/1995 | Golds et al. | |
| 5,423,860 A | 6/1995 | Lizardi et al. | |
| 5,458,601 A | 10/1995 | Young et al. | |
| 5,464,427 A | 11/1995 | Curtis et al. | |
| 5,480,403 A | 1/1996 | Lee et al. | |
| 5,486,197 A | 1/1996 | Le et al. | |
| 5,500,000 A | 3/1996 | Feagin et al. | |
| 5,505,735 A | 4/1996 | Li | |
| 5,522,843 A | 6/1996 | Zang | |
| 5,527,342 A | 6/1996 | Pietrzak et al. | |
| 5,545,180 A | 8/1996 | Le et al. | |
| 5,584,835 A | 12/1996 | Greenfield | |
| 5,584,860 A | 12/1996 | Goble et al. | |
| 5,607,432 A | 3/1997 | Fucci | |
| 5,630,824 A | 5/1997 | Hart | |
| 5,690,676 A | 11/1997 | DiPoto et al. | |
| 5,702,397 A | 12/1997 | Goble et al. | |
| 5,707,395 A | 1/1998 | Li | |
| 5,720,765 A | 2/1998 | Thal | |
| 5,723,013 A | 3/1998 | Jeanson et al. | |
| 5,725,529 A | 3/1998 | Nicholson et al. | |
| 5,728,136 A | 3/1998 | Thal | |
| 5,733,307 A * | 3/1998 | Dinsdale | 606/232 |
| 5,797,963 A | 8/1998 | McDevitt | |
| 5,827,291 A | 10/1998 | Fucci et al. | |
| 5,849,004 A | 12/1998 | Bramlet et al. | |
| 5,911,721 A | 6/1999 | Nicholson et al. | |
| RE36,289 E | 8/1999 | Le et al. | |
| 5,935,129 A | 8/1999 | McDevitt et al. | |
| 5,948,000 A | 9/1999 | Larsen et al. | |
| 5,948,001 A | 9/1999 | Larsen | |
| 5,957,953 A | 9/1999 | DiPoto et al. | |
| 6,010,525 A | 1/2000 | Bonutti et al. | |
| 6,086,608 A | 7/2000 | Ek et al. | |
| 6,117,162 A | 9/2000 | Schmieding et al. | |
| 6,129,763 A | 10/2000 | Chauvin et al. | |
| 6,136,032 A | 10/2000 | Viladot Perice et al. | |
| 6,146,387 A | 11/2000 | Trott et al. | |
| 6,149,669 A | 11/2000 | Li | |
| 6,152,934 A | 11/2000 | Harper et al. | |
| 6,159,235 A | 12/2000 | Kim | |
| 6,165,203 A | 12/2000 | Krebs | |
| 6,200,329 B1 | 3/2001 | Fung et al. | |
| 6,200,330 B1 | 3/2001 | Benderev et al. | |
| 6,206,886 B1 | 3/2001 | Bennett | |
| 6,214,007 B1 * | 4/2001 | Anderson | 606/304 |
| 6,228,096 B1 | 5/2001 | Marchand | |
| 6,267,766 B1 | 7/2001 | Burkhart | |
| 6,287,324 B1 | 9/2001 | Yarnitsky et al. | |
| 6,319,271 B1 | 11/2001 | Schwartz et al. | |
| 6,368,326 B1 | 4/2002 | Dakin et al. | |
| 6,436,124 B1 | 8/2002 | Anderson et al. | |
| 6,436,142 B1 | 8/2002 | Paes et al. | |
| RE37,963 E | 1/2003 | Thal | |
| 6,517,542 B1 | 2/2003 | Papay et al. | |
| 6,520,980 B1 | 2/2003 | Foerster | |
| 6,527,794 B1 | 3/2003 | McDevitt et al. | |
| 6,533,816 B2 | 3/2003 | Sklar | |
| 6,575,987 B2 | 6/2003 | Gellman et al. | |
| 6,585,730 B1 | 7/2003 | Foerster | |
| 6,616,694 B1 | 9/2003 | Hart | |
| 6,641,596 B1 * | 11/2003 | Lizardi | 606/232 |
| 6,652,563 B2 | 11/2003 | Dreyfuss | |
| 6,692,516 B2 | 2/2004 | West et al. | |
| 6,736,829 B1 | 5/2004 | Li et al. | |
| 6,783,527 B2 | 8/2004 | Drewry et al. | |
| 6,840,953 B2 | 1/2005 | Martinek | |
| 7,008,451 B2 * | 3/2006 | Justin et al. | 623/13.14 |
| 7,083,638 B2 | 8/2006 | Foerster | |
| 7,090,690 B2 | 8/2006 | Foerster et al. | |
| 7,416,556 B2 | 8/2008 | Jackson | |
| 7,491,217 B1 * | 2/2009 | Hendren et al. | 606/232 |
| 7,585,311 B2 | 9/2009 | Green et al. | |
| 7,604,640 B2 | 10/2009 | Kana | |
| 7,938,847 B2 | 5/2011 | Fanton et al. | |
| 8,118,835 B2 | 2/2012 | Weisel et al. | |
| 8,133,258 B2 | 3/2012 | Foerster et al. | |
| 8,137,381 B2 | 3/2012 | Foerster et al. | |
| 8,162,978 B2 | 4/2012 | Lombardo et al. | |
| 2001/0007072 A1 | 7/2001 | Steiner et al. | |
| 2002/0058966 A1 | 5/2002 | Tormala et al. | |
| 2002/0147463 A1 | 10/2002 | Martinek | |
| 2002/0161401 A1 | 10/2002 | Steiner | |
| 2002/0188301 A1 | 12/2002 | Dallara et al. | |
| 2003/0065361 A1 | 4/2003 | Dreyfuss | |
| 2003/0065390 A1 | 4/2003 | Justin et al. | |
| 2003/0083669 A1 | 5/2003 | Gleason | |
| 2003/0088272 A1 | 5/2003 | Smith | |
| 2003/0187446 A1 | 10/2003 | Overaker et al. | |
| 2003/0195563 A1 | 10/2003 | Foerster | |
| 2003/0208210 A1 | 11/2003 | Dreyfuss et al. | |
| 2004/0088004 A1 | 5/2004 | Rosch | |
| 2004/0093031 A1 | 5/2004 | Burkhart et al. | |
| 2004/0098050 A1 | 5/2004 | Foerster et al. | |
| 2004/0098052 A1 | 5/2004 | West et al. | |
| 2004/0133239 A1 | 7/2004 | Singhatat | |
| 2004/0138706 A1 | 7/2004 | Abrams et al. | |
| 2004/0138707 A1 | 7/2004 | Greenhalgh | |
| 2004/0225313 A1 | 11/2004 | Kanner et al. | |
| 2005/0033364 A1 | 2/2005 | Gregoire et al. | |
| 2005/0055052 A1 | 3/2005 | Lombardo et al. | |
| 2005/0107828 A1 | 5/2005 | Reese | |
| 2005/0216015 A1 | 9/2005 | Kreidler | |
| 2005/0222618 A1 | 10/2005 | Dreyfuss et al. | |
| 2005/0245932 A1 | 11/2005 | Fanton et al. | |
| 2006/0004364 A1 | 1/2006 | Green et al. | |
| 2006/0058800 A1 * | 3/2006 | Ainsworth et al. | 606/72 |
| 2006/0079904 A1 | 4/2006 | Thal | |
| 2006/0235413 A1 | 10/2006 | Denham | |
| 2006/0253119 A1 | 11/2006 | Berberich et al. | |
| 2006/0271060 A1 | 11/2006 | Gordon | |
| 2006/0282081 A1 | 12/2006 | Fanton et al. | |
| 2007/0005068 A1 | 1/2007 | Sklar | |
| 2007/0005069 A1 | 1/2007 | Contiliano et al. | |
| 2007/0038219 A1 | 2/2007 | Matthis et al. | |
| 2007/0142835 A1 | 6/2007 | Green et al. | |
| 2007/0167950 A1 | 7/2007 | Tauro et al. | |
| 2007/0203498 A1 * | 8/2007 | Gerber et al. | 606/72 |
| 2007/0218424 A1 | 9/2007 | Vuorisalo et al. | |
| 2007/0225736 A1 | 9/2007 | Zeiner et al. | |
| 2007/0288023 A1 | 12/2007 | Pellegrino et al. | |
| 2008/0009904 A1 | 1/2008 | Bourque et al. | |
| 2008/0015594 A1 | 1/2008 | Ritchart et al. | |
| 2008/0033460 A1 | 2/2008 | Ziniti et al. | |
| 2008/0051836 A1 | 2/2008 | Foerster et al. | |
| 2008/0077161 A1 | 3/2008 | Kaplan | |
| 2008/0125815 A1 | 5/2008 | Heaven et al. | |
| 2008/0133007 A1 | 6/2008 | Donnelly et al. | |
| 2008/0208253 A1 | 8/2008 | Dreyfuss et al. | |
| 2008/0215061 A1 | 9/2008 | Schumacher et al. | |
| 2008/0249567 A1 | 10/2008 | Kaplan | |
| 2008/0281353 A1 | 11/2008 | Aranyi et al. | |
| 2009/0112270 A1 | 4/2009 | Lunn et al. | |
| 2009/0312794 A1 | 12/2009 | Nason et al. | |
| 2009/0318965 A1 | 12/2009 | Burkhart | |
| 2009/0326545 A1 | 12/2009 | Schaffhausen | |
| 2010/0004683 A1 | 1/2010 | Hoof et al. | |
| 2010/0094355 A1 | 4/2010 | Trenhaile | |
| 2010/0318125 A1 | 12/2010 | Gerber et al. | |

FOREIGN PATENT DOCUMENTS

| | | |
|---|---|---|
| DE | 102008016607 A1 | 7/2009 |
| EP | 0611551 A1 | 2/1994 |
| EP | 1486171 | 12/2004 |
| EP | 1491162 A2 | 12/2004 |

(56) References Cited

FOREIGN PATENT DOCUMENTS

| | | |
|---|---|---|
| EP | 1491162 A2 | 12/2004 |
| EP | 1825817 A1 | 2/2007 |
| EP | 1825817 A1 | 8/2007 |
| EP | 1884198 | 4/2008 |
| JP | H04-250155 | 7/1992 |
| JP | 11506644 | 6/1999 |
| JP | H11-511357 | 10/1999 |
| JP | 2000-505324 | 5/2000 |
| JP | 2001-505081 | 4/2001 |
| JP | 2003505128 | 2/2003 |
| JP | 2003528648 | 9/2003 |
| JP | 2006-501003 | 1/2006 |
| JP | 2007532269 | 11/2007 |
| WO | 9639082 | 12/1996 |
| WO | 9706731 | 2/1997 |
| WO | 97/07743 | 3/1997 |
| WO | WO9729693 | 8/1997 |
| WO | 9835606 | 8/1998 |
| WO | 0106909 | 2/2001 |
| WO | 0110312 | 5/2001 |
| WO | WO0232345 A2 | 4/2002 |
| WO | WO0238059 A2 | 5/2002 |
| WO | WO0238059 A2 | 5/2002 |
| WO | WO2004062506 A1 | 7/2004 |
| WO | 2004096080 | 11/2004 |
| WO | 2005020832 | 3/2005 |
| WO | 2005037055 | 4/2005 |
| WO | WO2005102790 A1 | 11/2005 |
| WO | 2006/044491 | 4/2006 |
| WO | 2006/067548 | 6/2006 |
| WO | 2006060035 | 6/2006 |
| WO | 2006/078864 | 7/2006 |
| WO | 2007134248 | 11/2007 |
| WO | WO2008011417 A2 | 1/2008 |
| WO | WO2008054814 | 5/2008 |
| WO | WO2009055800 | 4/2009 |
| WO | WO2009055800 A1 | 4/2009 |

OTHER PUBLICATIONS

International Search Report and Written Opinion dated May 25, 2011.
Partial Internationai Search Report and Written Opinion for PCT/US2010/056107 Dated Feb. 23, 2011.
Office Action issued in corresponding Australian patent application No. 2008316604 mailed Feb. 5, 2013.
Office Action received for corresponding JP Application No. 2010-531316, Feb. 26, 2013.
Office Action for corresponding Japanese application No. 2012-538921 mailed Jul. 22, 2014.
Office Action for corresponding Japanese application No. 2013-164031 mailed Jul. 28, 2014.
Office Action for corresponding Chinese application No. 201080061088.8 mailed Jun. 23, 2014.
Office action received in corresponding European patent application No. 08 842 610.1-654 mailed Feb. 11, 2015.
Office action received in corresponding Russian patent application No. 2012122617/14(034396) mailed Feb. 19, 2015.
Office action received in corresponding Japanese patent application No. 2013-164031 mailed Feb. 18, 2015.
Office action received in corresponding Chinese patent application No. 201080061088.8 mailed Feb. 27, 2015.
Office action received in corresponding Japanese patent application No. 2012-538921 mailed Apr. 6, 2015.
Office action received in corresponding Australian patent application No. 2010319635 mailed Apr. 29, 2015.

\* cited by examiner

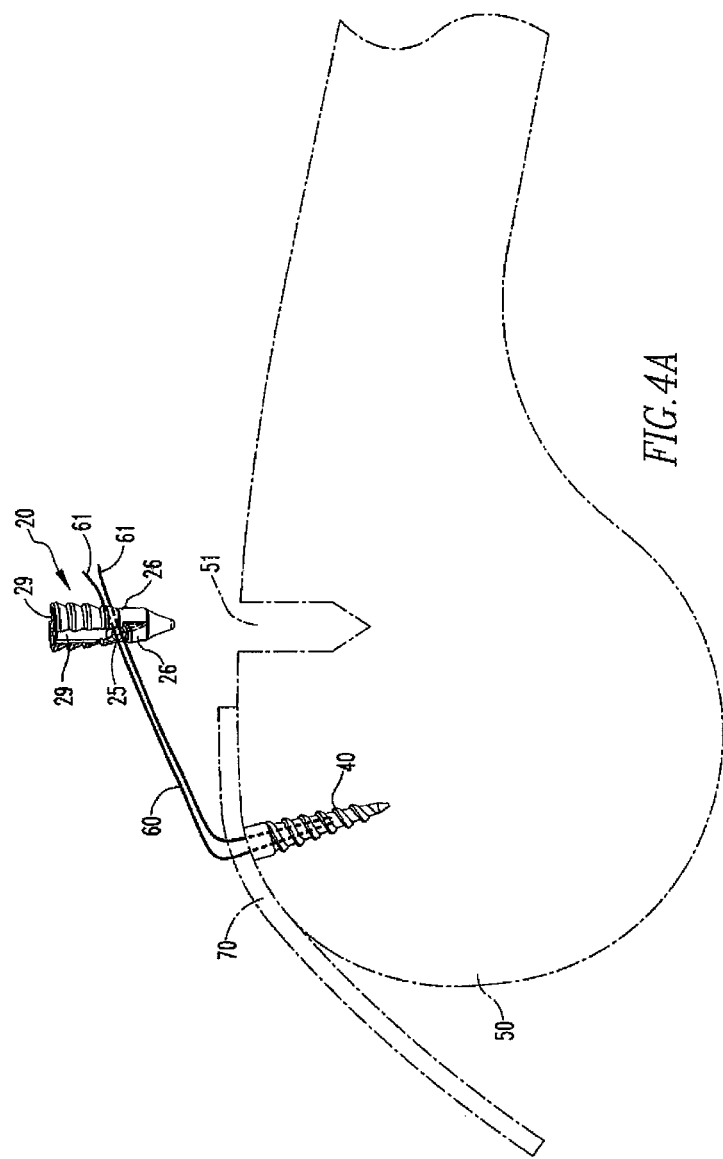

ANCHOR ASSEMBLY

CROSS-REFERENCE TO RELATED APPLICATIONS

This application claims the benefit of U.S. patent application Ser. No. 60/982,521 filed on Oct. 25, 2007 and U.S. patent application Ser. No. 60/986,342 filed on Nov. 8, 2007. The disclosures of each application are incorporated herein by reference in their entirety.

BACKGROUND

1. Field of Technology

The present disclosure relates to tissue repair, and more specifically, to an anchor assembly for securing tissue to bone.

2. Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

SUMMARY

In one aspect, the present disclosure relates to an anchor assembly. The anchor assembly includes an anchor defining a cavity and an opening to the cavity and an insertion member configured for arrangement within the anchor cavity. The insertion member includes a body having a proximal end portion and a flat distal end portion, and a head coupled to the proximal end portion of the body. The anchor includes protrusions located on an outer surface of the anchor, wherein the protrusions are configured to facilitate loading of a flexible member into the anchor. In an embodiment, the anchor assembly further includes a transverse through hole extending through the anchor. In another embodiment, the anchor assembly further includes at least two slots on an outer surface of the anchor, wherein the slots extend from the transverse through hole to a proximal portion of the anchor. In yet another embodiment, the anchor includes barbs on an outer surface of the body, wherein the barbs are intersected by the slots.

In a further embodiment, at least one flexible member, which may be a suture, is disposed within the through hole. In yet a further embodiment, a plurality of flexible members are disposed within the through hole. In yet an even further embodiment, the cavity includes threads. In an embodiment, the insertion member body includes threads, wherein the threads are configured for engagement with the threads of the cavity when the insertion member is arranged within the cavity. In another embodiment, the cavity extends into the through hole. In yet another embodiment, the head is configured for engagement with a delivery device. In a further embodiment, the insertion member is arranged within the anchor cavity such that the insertion member secures the flexible member in the through hole.

In another aspect, the present disclosure relates to a method of tissue repair. The method includes inserting a first anchor into bone, the first anchor having a flexible member coupled thereto; passing ends of the flexible member through the tissue; providing a second anchor defining a cavity and an opening to the cavity and a transverse through hole extending through the anchor; passing at least one end of the flexible member through the through hole of the second anchor; placing the second anchor into bone; providing an insertion member including a body having a proximal end portion and a flat distal end portion, and a head coupled to the proximal end portion of the body; and placing the insertion member within the anchor cavity of the second anchor to secure the flexible member in the through hole and the tissue to the bone.

In an embodiment, the method further includes tensioning the flexible member before placing the insertion member within the anchor cavity. In another embodiment, the method further includes moving the insertion member away from the through hole, tensioning the flexible member, and moving the insertion member back toward the through hole to resecure the flexible member in the through hole. In yet another embodiment, the second anchor includes protrusions, wherein the protrusions create paths in a wall of the bone when the second anchor is inserted into the bone. The paths allow the flexible member to slide through the second anchor when the second anchor is located in the bone.

In yet another aspect, the present disclosure relates to an anchor assembly. The anchor assembly includes an anchor defining a proximal portion, a distal portion, and an inner cavity; and an insertion member configured for arrangement within the inner cavity. The anchor includes barbs located on the proximal portion and protrusions located on the distal portion, wherein the protrusions are configured to facilitate loading of a flexible member into the anchor. In an embodiment, the insertion member includes a proximal end portion and a flat distal end portion.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 4A-4D show use of the anchor assembly of the present disclosure in repairing tissue.

DETAILED DESCRIPTION OF THE EMBODIMENTS

The following description of the preferred embodiments is merely exemplary in nature and is in no way intended to limit the disclosure, its application, or uses.

Figure 1:
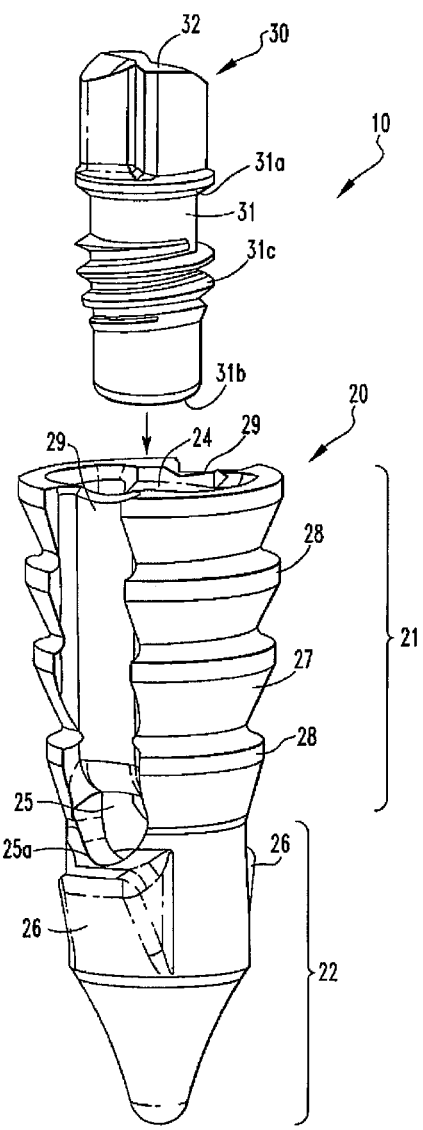
FIG. 1 shows an exploded view of the anchor assembly of the present disclosure.
Figure 2:
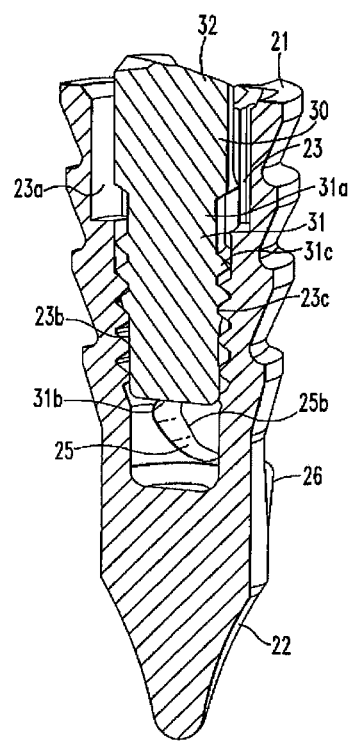
FIG. 2 shows a cross-sectional view of the anchor assembly of the present disclosure.
Figure 3:
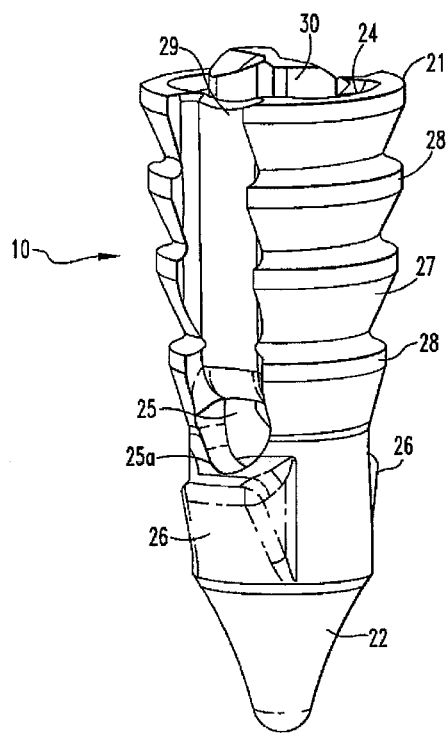
FIG. 3 shows a front view of the anchor assembly of the present disclosure.

FIGS. 1-3 show the anchor assembly 10 of the present disclosure. The assembly 10 includes the anchor 20 and the insertion member 30. The anchor 20 includes a proximal portion 21, a distal portion 22, and an inner cavity 23. An opening 24 to the cavity 23 is located at the proximal portion 21 of the anchor 20. A transverse through hole 25 is located between the proximal and distal portions 21,22 and extends through the anchor 20. Openings 25a,b are located at each end of the through hole 25. Located below each opening 25a,b is a protrusion 26. The protrusions 26 facilitate loading of a flexible member, such as a suture, through the through hole 25, and allow for the creation of a path in the wall of a bone hole when the anchor 20 is inserted into bone hole, as will be further described below. The outer surface 27 of the proximal portion 21 also includes barbs 28 for substantially reducing the possibility of removal of the anchor 20 when inserted into bone, as will be further described below. The outer surface 27 also includes slots 29 extending from the openings 25a,b of the through hole 25 to the proximal portion 21 of the anchor 20. The slots 29 intersect the barbs 28 and are configured for housing of the suture after positioning of the anchor 20 in bone, as further described below. As shown in FIG. 2, the cavity 23 extends into the through hole 25 and includes a proximal portion 23a and a threaded distal portion 23b for receipt of the insertion member 30, as will be further described below.

The insertion member 30 includes a body 31, having a proximal end portion 31a and a flat distal end portion 31b, and a head 32 coupled to the proximal end portion 31a. The head 32 is configured for engagement with a delivery tool and the body 31 includes threads 31c that are configured for engagement with the threads 23c of the cavity 23 when the insertion member is arranged within the cavity 23, as shown in FIG. 2.

Figure 4B:
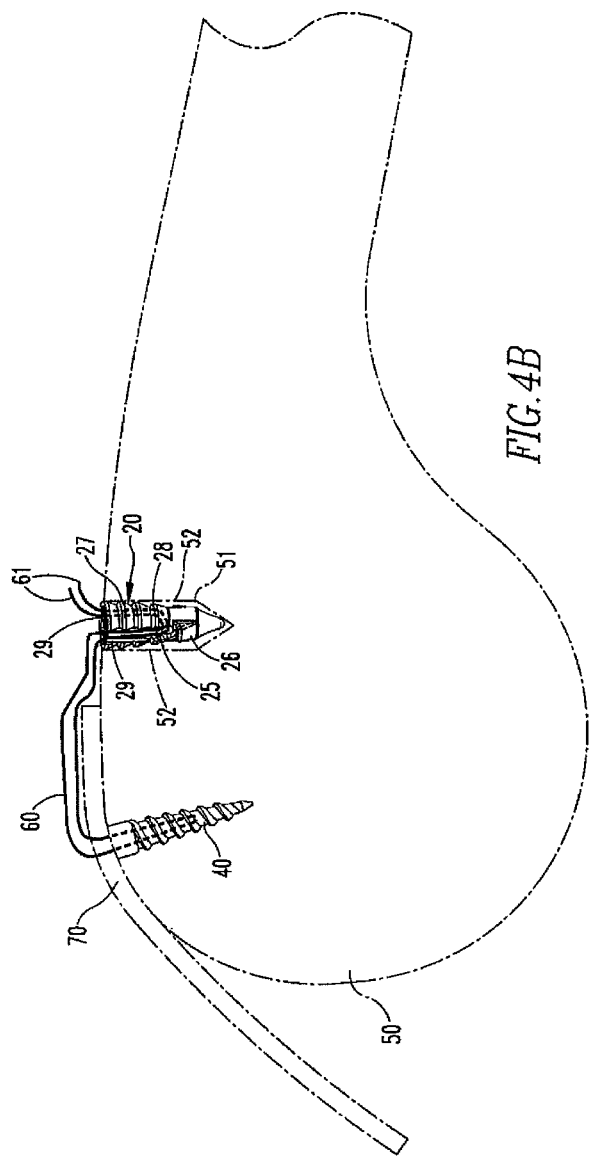

The anchor 10 of the present disclosure may be used in conjunction with another anchor to repair soft tissue. FIGS. 4A-4D show the anchor assembly 10 in use during arthroscopic repair of the rotator cuff. However, the anchor assembly 10 may be used in the repair of soft tissue in other parts of the body. FIG. 4A shows a first anchor 40 that has been inserted into the lateral aspect of a bone 50, such as a humeral bone. The anchor 40, which has a flexible member 60, such as a suture, coupled thereto is inserted into the bone 50, a soft tissue 70, such as a rotator cuff tendon, is placed on the bone 50 to be located adjacent to the anchor 40, and the ends 61 of the flexible member 60 are placed through the soft tissue 70.

Figure 4C:
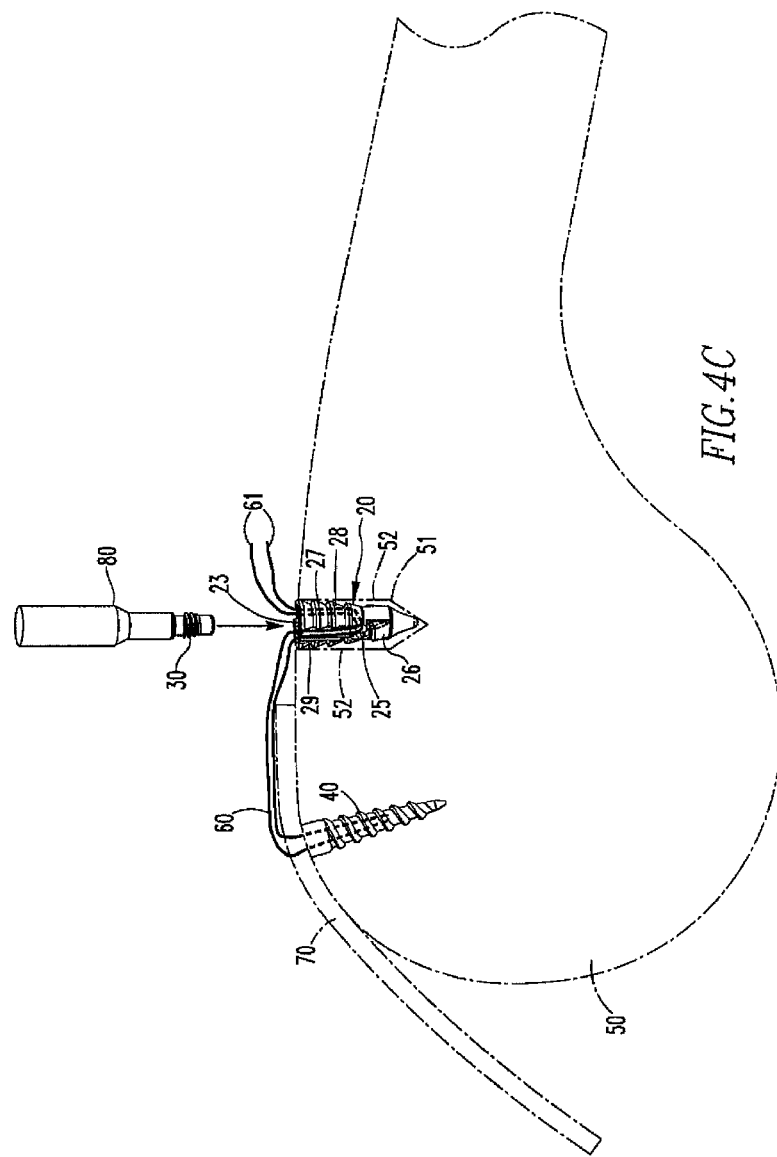
Figure 4D:
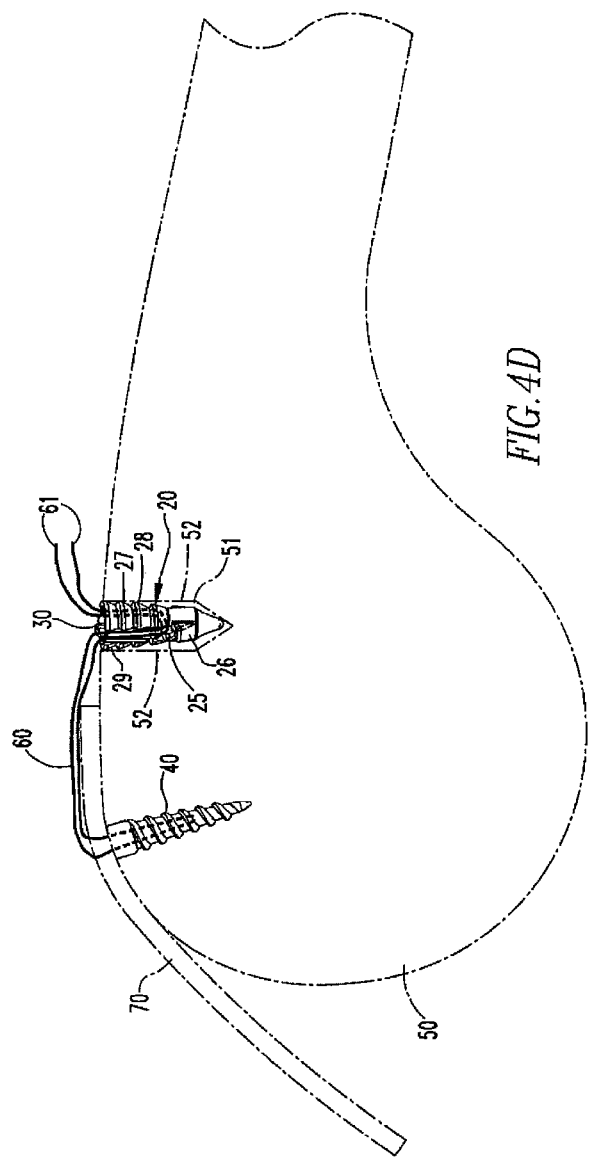

Next, at least one end 61 of the flexible member 60 is passed through the transverse through hole 25 of a second anchor, such as the anchor 20 of the present disclosure, and the anchor 20 is subsequently placed into a previously drilled hole 51 in the medial aspect of the bone 50, as shown in FIG. 4B, such that the flexible member 60 is housed within the transverse through hole 25 and both slots 29 of the anchor 20 and the ends 61 extend out of the hole 51. The anchor 20 is advanced into the hole 50 in an axially-oriented manner by tapping on the end of a delivery tool (not shown) that is used to deliver the anchor 20 into the hole 51. FIGS. 4B-4D show spaces between the outer surface 27 of the anchor 20 and the walls 52 of the hole 51. However, the diameter of the hole 51 will be sized such that the barbs 28 of the anchor 20 will abut the walls 52, and most likely extend through the walls 52 and into the bone 50, in order to substantially reduce the possibility of anchor removal. In addition, due to the hole diameter, the protrusions 26 located below the openings 25a,b create a path (not shown) in the wall of the bone hole 51 when the anchor 20 is inserted into hole 51. This path allows the suture 60 to slide when through the anchor 20 when the anchor 20 is located within the hole 51.

After placement of the anchor 20 into the hole 51, the ends 61 of the flexible member 60 may be pulled to provide a preferred amount of tension on the flexible member 60 and the soft tissue 70. This tension on the flexible member 60 can be seen in FIGS. 4C-D, especially when comparing these figures to FIG. 4B. The insertion member 30 is subsequently placed in the anchor cavity 23 in a rotary manner, via a delivery tool 80, to secure the flexible member 60 in the through hole 25 and the tissue 70 to the bone 50. The insertion member 30 may be removed from the cavity 23 to re-tension the flexible member 60 and then replaced within the cavity 23 to re-secure the flexible member 60 in the through hole 25.

The components of the anchor assembly 10 and the first anchor 40 are made from a bioabsorbable polymer material via an injection molding process. However, other materials and processes may be used. In addition, the suture material is made from a bioabsorbable polymer material, but other material may be used. Also, the initial anchor, such as the first anchor 40 shown above, may include more than one suture and the sutures may be secured together at one attachment point, such as within the second anchor 20 shown above, or independently at more than one attachment point. Furthermore, the outer surface 27 of the anchor 20 may include features other than barbs 28 to reduce the possibility of removal of the anchor 20 and the barbs 28 may extend the entire length or a partial length of the anchor 20. Similarly, the body 31 of the insertion member 30 and the cavity 23 of the anchor 20 may include features other than threads to facilitate insertion and removal of the insertion member 30 and the threads may extend the entire length or a partial length of the body 31 and cavity 23. Also, for the purposes of this disclosure, the through hole 25 is located between the proximal 21 and distal 22 portions, but may be located anywhere along the length of the anchor 20.

The anchor assembly 10 of the present disclosure allows a surgeon to load a suture from a previously placed anchor and secure the suture in the assembly 10 at a preferred tension. In addition, the assembly 10 allows the tension on the suture to be adjusted with tactile feedback. Furthermore, the assembly allows for one or more sutures to be secured together at one attachment point, such as described above with the second anchor 20, or independently at several attachment points. This allows for a large area of contact between the tissue and the bone and results in a better repair.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchor assembly comprising:
  an anchor defining a cavity comprising a proximal portion and a distal portion, the proximal portion including a larger diameter than the distal portion, an opening to the cavity, and a transverse through hole extending through the anchor, the through hole including openings at each end of the through hole that open to an outer surface of the anchor, the cavity extending into the through hole; and
  an insertion member configured for arrangement within the anchor cavity, the insertion member including a body having a proximal end portion and a flat distal end portion, and a head coupled to the proximal end portion of the body,
wherein the anchor includes protrusions located on an outer surface of the anchor and below the through hole openings, the protrusions tapered along their lengths and extending away from the outer surface of the anchor, the protrusions arranged on the outer surface such that non-tapered areas are located between the protrusions, the protrusions configured to facilitate loading of a flexible member into the anchor, wherein the non-tapered areas are rounded.

2. The anchor assembly of claim 1 further comprising at least two slots on an outer surface of the anchor.

3. The anchor assembly of claim 2 wherein the anchor includes barbs on an outer surface of the body.

4. The anchor assembly of claim 1 wherein at least one flexible member is disposed within the through hole.

5. The anchor assembly of claim 1 wherein the cavity includes threads.

6. The anchor assembly of claim 5 wherein the insertion member body includes threads, the threads configured for engagement with the threads of the cavity when the insertion member is arranged within the cavity.

7. The anchor assembly of claim 1 wherein the head is configured for engagement with a delivery device.

8. The anchor assembly of claim 4 wherein the insertion member is arranged within the anchor cavity such that the insertion member secures the flexible member in the through hole.

9. The anchor assembly of claim 4 wherein a plurality of flexible members are disposed within the through hole.

10. The anchor assembly of claim 4 wherein the flexible member includes a suture.

11. The anchor assembly of claim 2 wherein the slots extend from the transverse through hole to a proximal portion of the anchor.

12. The anchor assembly of claim 3 wherein the barbs are intersected by the slots.

13. The anchor assembly of claim 1 wherein the through hole openings are in alignment with each other.

14. The anchor assembly of claim 5 wherein the distal portion of the cavity is threaded and the proximal portion of the cavity is non-threaded.

15. An anchor assembly comprising:
an anchor defining a proximal portion, a distal portion, and an inner cavity comprising a proximal portion and a distal portion, the proximal portion including a larger diameter than the distal portion, and a transverse through hole extending through the anchor, the through hole including openings at each end of the through hole that open to an outer surface of the anchor, the cavity extending into the through hole; and
an insertion member configured for arrangement within the inner cavity, wherein the anchor includes barbs located on the proximal portion and protrusions located on the distal portion and below the through hole openings, the protrusions tapered along their lengths and extending away from an outer surface of the anchor, the protrusions arranged on the outer surface such that non-tapered areas are located between the protrusions, the protrusions configured to facilitate loading of a flexible member into the anchor, wherein the non-tapered areas are rounded.

16. The anchor assembly of claim 15 wherein the insertion member includes a proximal end portion and a flat distal end portion.

17. The anchor assembly of claim 15 wherein the through hole openings are in alignment with each other.

18. The anchor assembly of claim 15 wherein the distal portion of the cavity is threaded and the proximal portion of the cavity is non-threaded.

19. An anchor assembly comprising:
an anchor including a proximal portion and a closed-ended distal portion, the anchor defining a cavity comprising a proximal portion and a distal portion, the proximal portion including a larger diameter than the distal portion, an opening to the cavity, and a transverse through hole extending through the anchor, the through hole including openings at each end of the through hole that open to an outer surface of the anchor, the cavity extending into the through hole, wherein the anchor includes protrusions located on an outer surface of the anchor and below the through hole openings, the protrusions tapered along their lengths and extending away from the outer surface of the anchor, the protrusions arranged on the outer surface such that rounded non-tapered areas are located between the protrusions; and
an insertion member configured for arrangement within the anchor cavity, the insertion member including a body having a proximal end portion and a flat distal end portion, and a head coupled to the proximal end portion of the body, the head integral with the body and of a larger diameter than the body.

20. The anchor assembly of claim 19 wherein the through hole openings are in alignment with each other.

21. The anchor assembly of claim 19 wherein the head is closed-ended.

22. The anchor assembly of claim 19 wherein the insertion member body includes threads on its outer surface, non-threaded areas located above and below the threads, the non-threaded areas including the same diameter.

23. The anchor assembly of claim 19 wherein the distal portion of the cavity is threaded and the proximal portion of the cavity is non-threaded.

24. An anchor assembly comprising:
an anchor including a proximal portion and a closed-ended distal portion, the anchor defining a cavity comprising a proximal portion and a distal portion, the proximal portion including a larger diameter than the distal portion, an opening to the cavity, and a transverse through hole extending through the anchor, the through hole including openings at each end of the through hole that open to an outer surface of the anchor, the cavity extending into the through hole, wherein the anchor includes protrusions located on an outer surface of the anchor and below the through hole openings, the protrusions tapered along theirs lengths and extending away from the outer surface of the anchor, the protrusions arranged on the outer surface such that rounded non-tapered areas are located between the protrusions; and
an insertion member configured for arrangement within the anchor cavity, the insertion member including a body having a proximal end portion and a flat distal end portion, and a head coupled to the proximal end portion of the body, the head integral with the body and of a larger diameter than the body,
wherein at least one flexible member is disposed within the through hole, the insertion member arranged within the anchor cavity such that the insertion member secures the flexible member in the through hole.

25. The anchor assembly of claim 24 wherein the through hole openings are in alignment with each other.

26. The anchor assembly of claim 24 wherein the head is closed-ended.

27. The anchor assembly of claim 24 wherein the insertion member body includes threads on its outer surface, non-threaded areas located above and below the threads, the non-threaded areas including the same diameter.

28. The anchor assembly of claim 24 wherein the distal portion of the cavity is threaded and the proximal portion of the cavity is non-threaded.

\* \* \* \* \*